US00PP30072P3

(12) United States Plant Patent
Biancheri

(10) Patent No.: US PP30,072 P3
(45) Date of Patent: Jan. 8, 2019

(54) ***RANUNCULUS* PLANT NAMED 'ABEPONA'**

(50) Latin Name: *Ranunculus asiaticus*
Varietal Denomination: ABEPONA

(71) Applicant: Alberto Biancheri, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 15/731,518

(22) Filed: Jun. 20, 2017

(65) Prior Publication Data

US 2018/0020589 P1 Jan. 18, 2018

(30) Foreign Application Priority Data

Jul. 13, 2016 (QZ) ..... PBR 2016/1772

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02; A01H 5/00; A01H 6/72
See application file for complete search history.

(56) References Cited

PUBLICATIONS

Biancheri Creazioni for Igloo, retrieved on May 16, 2018, retrieved from the Internet at https://www.bianchericreazioni.it/scheda-91-igloo, one page (Year: 2018).*
Easy to Grow Bulbs Italian *Ranunculus* Cloni Pon-Pon Igloo, retrieved on May 16, 2018, retrieved from the Internet at https://www.easytogrowbulbs.com/collections/italian-ranunculus/products/italian-ranunculus-cloni-pon-pon-igloo?variant=45370921292, 2 pp. (Year: 2018).*
The Hollywood Reporter. Oscars: A Guide to the 88th Academy Awards Feb. 27, 2016, retrieved on May 16, 2018, retrieved from the Internet at https://www.hollywoodreporter.com/lists/oscars-guide-88th-academy-awards-870214/item/key-info-oscars-guide-2016-870370, 2 pp. (Year: 2016).*
Missouri Botanical Garden for *Ranunculus asiaticus*, retrieved on May 16, 2018, retrieved from the Internet at http://www.missouribotanicalgarden.org/PlantFinder/PlantFinderDetails.aspx?kempercode=a471, 2 pp. (Year: 2018).*

* cited by examiner

*Primary Examiner* — June Hwu
(74) *Attorney, Agent, or Firm* — Cassandra Bright

(57) ABSTRACT

A new and distinct *Ranunculus* cultivar named 'ABEPONA' is disclosed, characterized by a unique combination of colors in the corolla, including shades of green and white. The petals are deeply undulating. Vase life of the cut flower is exceptionally long and the corolla is round when fully open. The new variety is a *Ranunculus*, normally produced as a cut flower and potentially useful as an ornamental plant.

2 Drawing Sheets

Latin name of the genus and species: *Ranunculus asiaticus*.

Variety denomination: 'ABEPONA'.

BACKGROUND OF THE INVENTION

The new *Ranunculus* cultivar is a product of a planned breeding program conducted by the inventor, Alberto Biancheri in Camporosso Mare, Italy. The cross resulting in this new variety was made during 2009.

The seed parent is the, unpatented, proprietary variety referred to as *Ranunculus* 'PPB109-07/2'. The pollen parent is the unpatented, proprietary variety referred to as *Ranunculus* 'PPB45-07/2'. The new variety was discovered in 2012 by the inventor in a group of seedlings resulting from the 2008 crossing, in a research greenhouse in Camporosso Mare, Italy.

Asexual reproduction of the new cultivar was first performed by vegetative division of buds sprouting from the tuberous root of the selected plant. Subsequent propagation has been performed by tissue culture. First propagation took place at a research greenhouse in Camporosso Mare, Italy in 2012 and has shown that the unique features of this cultivar are stable and reproduced true to type in multiple successive generations.

SUMMARY OF THE INVENTION

The cultivar 'ABEPONA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABEPONA' These characteristics in combination distinguish 'ABEPONA' as a new and distinct *Ranunculus* cultivar:

1. Unique combination of colors in the corolla, including white and shades of green.
2. Rounded shape of the corolla when it is fully open.
3. Deeply ruffled and textured petals.
4. Exceptionally long vase life.
5. High productivity.

PARENT COMPARISON

Plants of the new cultivar 'ABEPONA' are similar to plants of the seed parent, in most horticultural characteristics, however, plants of the new cultivar 'ABEPONA' differ in the following;

1. Flower size.

Plants of the new cultivar 'ABEPONA' are similar to plants of the pollen parent, in most horticultural characteristics, however, plants of the new cultivar 'ABEPONA' differ in the following;

1. The new variety has a different flower color than the pollen parent.
2. Flower size.

COMMERCIAL COMPARISON

Plants of the new cultivar 'ABEPONA' are comparable to the commercial variety *Ranunculus* 'ABATLAUA', U.S. Plant patent application Ser. No. 15/731,516, filed concurrently. The two *Ranunculus* varieties are similar in most horticultural characteristics; however, the new variety 'ABEPONA' differs in the following:

1. Combination of colors in the corolla; 'ABEPONA' has a corolla made up of shades of green and white, corolla color of 'ABATLAUA' is shades of purple and green.

BRIEF DESCRIPTION OF THE PHOTOGRAPHS

Figure 1:
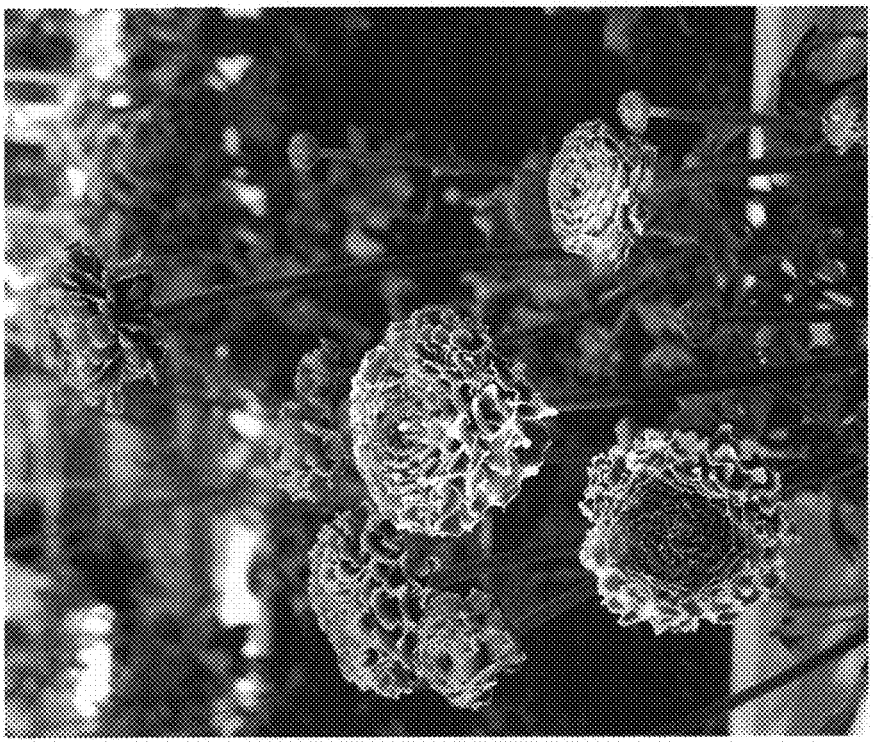

The accompanying photograph in FIG. 1 illustrates in full color flowering plants of the new variety at approximately five months old, grown in a greenhouse.

Figure 2:
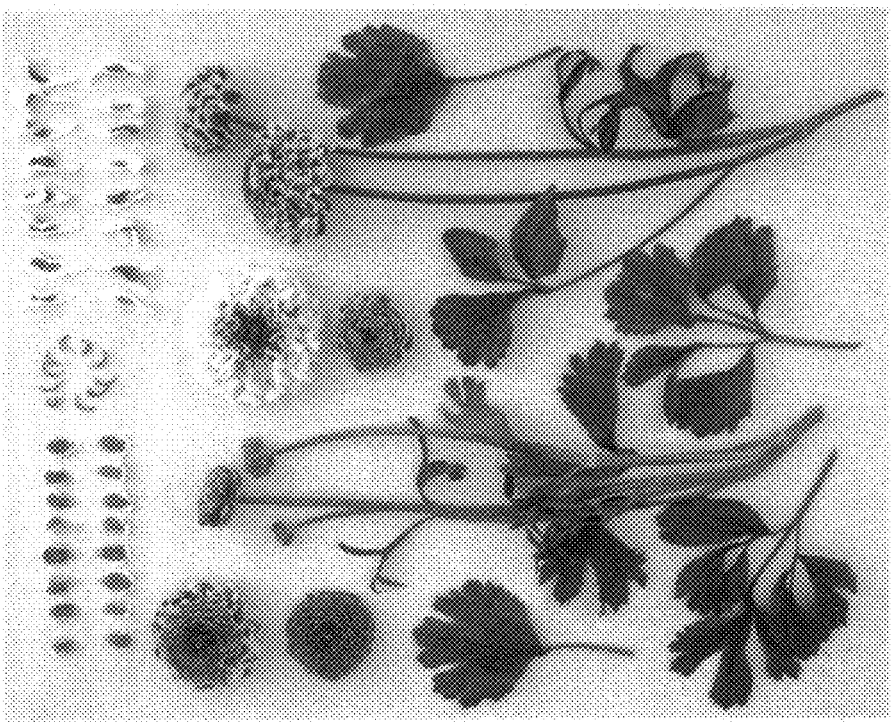

FIG. 2 illustrates a close up of plant parts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 'ABEPONA' plants grown in a greenhouse Camporosso Mare, Italy. The plant described has been cultivated under glass, planted in the months of September and described in the month of February. One must always refer to these conditions of season and culture, when considering the present description. By reason of different climate or culture conditions, differences may arise between certain characteristics of the plant and the corresponding characteristics of the description. It should be considered as normal and do not modify the essence of the present invention because it will possible to identify the plant by means of the totality of the characteristics given in the description. The tuberous root has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types. Botanical classification: *Ranunculus asiaticus* 'ABEPONA'.

Propagation:

*Time to rooting.*—15 days at approximately 10-12° C.

*Time to produce a rooted plantlet.*—20 days.

*Root description.*—Tuberous roots. Tuber quantity varies with age and environmental conditions, the average range can be 5 to 10. Color is white to tan, not accurately measured with an R.H.S. chart.

Plant:

*Growth habit.*—Herbaceous perennial, robust plant, semi-erect vegetation.

*Height to top flower.*—60 to 65 cm.

*Plant spread.*—50 to 60 cm.

*Growth rate.*—Medium.

*Branching characteristics.*—Main floral stems grow from a basal rosette with 1 or 2 lateral branches, each one of which has a flower.

*Length of lateral branches.*—50 to 60 cm.

*Diameter of lateral branches.*—0.5 to 0.8 cm.

*Texture of lateral branches.*—Slightly tomentose.

*Internode length.*—Internodes are extremely close together forming a basal rosette.

*Strength of lateral branches.*—Medium.

*Color of lateral branches.*—Yellow Green (RHS 144A).

*Angle of branches.*—15° to 20°.

*Number of leaves per lateral branch.*—Usually 2.

Foliage:

*Leaf.*—The leaves, usually numerous, have a marked heterophyllia (significant variation in leaf shape, size and arrangement on a same plant), Simple, biternate and ternate leaves appear on the same plant, in relation to the degree of development (young leaf and mature leaf) and their position on the plant (basal leaf — leaf at the base of the plant — and cauline leaf — leaf inserted at the nodes of the floral stems).

*Leaf at the base of the plant.*—Arrangement: Simple (young leaf, YL); Biternate (mature leaf, ML). Average Length: 10 to 16 cm. Average Width: 15 to 22 cm. Overall Shape of blade: Obovate (young leaf); Palmatipartite (mature leaf). Dissected leaves, describe lobes, quantity of dissection: Young leaves are generally not lobed; mature leaves are generally divided in 3 parts, each one of which is further divided in more lobes. Apex: Rounded. Base: Rounded. Attachment: Petiolate. Margin: Dentate. Texture of top surface: Slightly tomentose. Texture of bottom surface: Slightly tomentose. Appearance of top surface: Glossy. Appearance bottom surface: Very glossy. Leaf internode length: The internodes are extremely close together, forming a basal rosette. Color: Young foliage upper side: Green (RHS 137A). Young foliage under side: Yellow Green (RHS 146B). Mature foliage upper side: Green (RHS 137A). Mature foliage under side: Yellow Green (RHS 146B).

*Venation.*—Type: Dichotomous; plunging in to the limb at the upper surface; raised on the limb at the lower surface. Venation color upper side: Yellow Green (RHS 144A). Venation color under side: Yellow Green (RHS 144A).

*Petiole.*—Petiole: Long, tubular, rigid. Length: 18 to 20 cm. Diameter: 0.4 to 0.7 cm. Pubescence: Slightly tomentose. Color: Yellow Green (RHS 144A).

*Leaf inserted at the nodes of the floral stems (sl).*—Arrangement: Bifoliate/Biternate. Average Length: 18 to 20 cm. Average Width: 10 to 15 cm. Overall Shape of blade: Palmatipartite. Dissected leaves, describe lobes, quantity of dissection: Generally divided in 2 parts, each one of which is further divided in many deeply incised lobes. Apex: Acute. Base: Acute. Attachment: Floral stems. Margin: Dentate. Texture of top surface: Slightly tomentose. Texture of bottom surface: Slightly tomentose. Appearance of top surface: Glossy. Appearance bottom surface: Glossy. Leaf internode length: 4 to 8 cm. Color: foliage upper side: Green (RHS 137B). foliage under side: Green (RHS 138B). Venation: Type: Longitudinal, deeply plunging in to the limb at the upper surface and very raised on the limb at the lower surface. Venation color upper side: Yellow Green (RHS 144A). Venation color under side: Yellow Green (RHS 144A). Petiole: Petiole: Slightly flat, rigid. Length: 8 to 10 cm. Diameter: 0.7 to 0.9 cm. Pubescence: Slightly tomentose. Color: Yellow Green (RHS 144A).

Flower:

*Bloom period.*—Winter to Spring.

*Vase life* (*cut flower*).—15-20 days.

*Persistent or self-cleaning.*—Self-Cleaning.

*Number of flowers per plant.*—8-10.

*Bud.*—Closed bud (CB): Shape: Flattened globular. Length: 1.0 to 1.6 cm. Diameter: 1.3 to 2.0 cm. Color: Green (RHS 137B). Slightly open bud (OB): Shape: Flattened globular. Length: 1.8 to 2.2 cm. Diameter: 2.0 to 2.3 cm. Color: Yellow Green (RHS N144C); Yellow Green (RHS N145A) near the margin.

*Flower size* ($of_{1,2}$).—Diameter: 8 to 12 cm. Height: 3 to 4 cm.

*Corolla* ($of_{1,2}$).—Round, regular, in the form of a flat section with slightly festooned edges. Petals: Arrangement: Imbricated, disposed on the receptacle in very tight verticils. The size of the petals is quite variable, according to the position in the corolla, decreasing from the exterior toward the center. The average size of fully developed petal is as follows: Length: 3.5 to 4.5 cm. Width: 2.5 to 3.0 cm. Quantity: Double flower, petals are very numerous typically 150 to 200. Texture: Silky, thin, resistant, slightly tomentose on upper and lower surfaces. Apex: Flat. Shape: Truncate. Margin: Sinuate. Aspect: Trapezoid, concave, reflexed when flower is fully opened. Color when opening (CF): Upper surface: Yellow Green (RHS 144A); Margin near Green-White 157D. Lower surface: Yellow Green (RHS 144A); Margin near Green-White 157D. Color Fully opened (OF): Upper surface ($PU_1$): White 155C from the margin towards the center and along the venations; Yellow Green (RHS 144A). Lower surface ($PL_1$): White 155D from the margin towards the center and along the venations; Yellow Green (RHS 144A). Other cultural improvements or features: In this variety, the colors of the corolla could present a lack of White tones and an increase of Green tones. This is already noticeable in the flowers that are opening and is present in those that are wide open (OF2; PU2, PL2). This variation of color, partially typical of this variety, is accentuated in particular growing conditions, in relation to light exposure, to the temperature and to the different composition of fertilizers used by the various farms.

*Calyx to sepals* (*s*).—Quantity per flower: 10 to 12. Shape: Concave, moderately incurved. Length: 1.5 to 2.0 cm. Width: 0.3 to 0.5 cm. Apex: Acute. Base: Flat to slightly rounded. Margin: Entire. Texture: Lower surface is tomentose; Upper surface is glabrous. Color Upper Surface: Green (RHS 138B). Color Lower Surface: Green (RHS 137C).

*Peduncle.*—None.

*Pedicel.*—Length: 50 to 55 cm. Diameter: 1.2 to 1.6 cm. Color: Yellow Green (RHS 144A). Orientation: Upright, straight, rigid. Pubescence: Slightly tomentose.

*Fragrance.*—None.

Reproductive organs:

*Androecium.*—Stamens: Rarely occurring, irregular. Anther shape: Oblong. Anther length: 3 to 4 mm. Anther color: Yellow (RHS 7A). Pollen quantity: Scarce.

*Gynoecium.*—The pistils are numerous, irregular in quantity, short, fused together at the center of the corolla in a Yellow Green (RHS 144B) and Yellow Green (RHS 154A), dome-shaped apocarpous gynoecium.

*Nectar gland.*—Absent.

Other characteristics:

*Seeds and fruits.*—Seeds and fruit production not observed.

*Disease and pest resistance.*—Neither resistance nor susceptibility to normal diseases and pests of *Ranunculus* has been observed.

*Temperature tolerance.*—Upper and lower temperature tolerance not observed, plants have been grown in a climate controlled greenhouse. *Ranunculus asiaticus* typically tolerates temperatures within USDA Zones 7 to 11.

What is claimed is:

1. A new and distinct cultivar of *Ranunculus* plant named 'ABEPONA' as herein illustrated and described.

* * * * *